United States Patent
Booker et al.

(10) Patent No.: US 6,795,189 B2
(45) Date of Patent: Sep. 21, 2004

(54) UNIVERSAL MICROPLATE ANALYZER

(75) Inventors: David Dickson Booker, Chicago, IL (US); Robert E. Fischer, Westlake Village, CA (US); Michael P. Newell, Thousand Oaks, CA (US); David W. Kappel, San Diego, CA (US); Scott Moritz, Villa Park, IL (US); Jerome E. Oleksy, Park Ridge, IL (US)

(73) Assignee: Packard Instrument Company, Downers Grove, IL (US)

( * ) Notice: Subject to any disclaimer, the term of this patent is extended or adjusted under 35 U.S.C. 154(b) by 193 days.

(21) Appl. No.: 09/872,953

(22) Filed: Jun. 1, 2001

(65) Prior Publication Data

US 2002/0043626 A1 Apr. 18, 2002

Related U.S. Application Data

(60) Provisional application No. 60/211,560, filed on Jun. 15, 2000.

(51) Int. Cl.[7] .......................... G01N 21/25; G01J 3/30; F21V 9/16
(52) U.S. Cl. ................ 356/417; 356/317; 356/318; 250/458.1; 250/459.1
(58) Field of Search .................. 356/417, 317, 356/318; 250/458.1, 459.1

(56) References Cited

U.S. PATENT DOCUMENTS

| | | | |
|---|---|---|---|
| 4,076,420 A | 2/1978 | De Maeyer et al. | 356/73 |
| 4,305,660 A | 12/1981 | Kallet | 356/73 |
| 4,730,922 A | 3/1988 | Bach et al. | 356/73 |
| 6,042,785 A | 3/2000 | Harju | 422/52 |
| 6,084,680 A | 7/2000 | Tuunanen et al. | 356/417 |
| 6,144,455 A | 11/2000 | Tuunanen et al. | 356/402 |
| 6,317,207 B2 * | 11/2001 | French et al. | 356/317 |
| 6,326,605 B1 * | 12/2001 | Modlin et al. | 250/214 SW |
| 6,483,582 B2 * | 11/2002 | Modlin et al. | 356/317 |

* cited by examiner

*Primary Examiner*—Frank G. Font
*Assistant Examiner*—Khaled Brown
(74) *Attorney, Agent, or Firm*—Jenkens & Gilchrist

(57) ABSTRACT

A universal microplate analyzer capable of carrying out measurements on samples contained in the wells of microplates by fluorescence, absorbance, luminescence employs at least two light sources and optical fiber channels for directing excitation light to the sample wells. Flexibility of operation is provided by arrays of mirrors, apertures, and polarizers which can be positioned as required for the analysis to be carried out.

48 Claims, 11 Drawing Sheets

UNIVERSAL MICROPLATE ANALYZER

This application claims the benefit of Provisional Application No. 60/211,560, filed Jun. 15, 2000.

BACKGROUND OF THE INVENTION

The invention relates generally to equipment used to analyze chemical and biological samples in multiwell containers, commonly called microplates. Currently, they have up to 1536 wells in an array measuring about 3.4 by 5 inches (87×127 mm). Many types of analysis are possible, each one employing a light detector to determine the amount of light emitted from a sample in one of the wells. In general, analyses or measurements are made by fluorescence, absorbance, or luminescence. Most analyses involve measuring the light emitted in response to excitation light directed into the sample or as the result of the introduction of chemical reagents. The present invention provides a means for carrying out each of these general types of analysis in a single instrument, a commercial embodiment of which is designated the Fusion™ Universal Microplate Analyzer by its manufacturer, the Packard Instrument Company.

Other analyzers which are able to carry out similar measurements on chemical and biological samples are disclosed in a large number of patents. Representative of more recent patents are the analyzers discussed in the following.

U.S. Pat. No. 6,042,785 assigned to Wallac OY shows an instrument capable of performing various spectrographic measurements. Two types of excitation light sources are used and two detectors for receiving light emitted from the sample, either passing through a mirror or through an aperture.

LJL Bio Systems in U.S. Pat. Nos. 6,097,028 and 6,071,748 shows a multifunctional analyzer which employs a plurality of excitation light sources and emitted light detectors. Optical switches are included to direct the excitation light and emission light to and from the sample. A feature of the instrument is its ability to limit the light to a "sensed volume" away from the walls of the sample container.

Lab Systems OY in U.S. Pat. Nos. 6,144,455 and 6,084,680 shows a fluorometer in which a partly reflective mirror has a plurality of areas transparent to excitation and emitted light and a plurality of areas which are non-transparent to excitation and emitted light.

The present inventors have sought to develop a multi-purpose analyzer capable of carrying out various types of measurements in an effective and efficient manner. Their universal microplate analyzer is described below.

SUMMARY OF THE INVENTION

In one aspect, the invention is a universal microplate analyzer, as shown in the accompanying illustrations and described below. The analyzer includes the following features:

Analyses which can be carried out on samples include fluorescence, absorption, and luminescence.

Measurements may be made in at least four modes:
excitation light is introduced into the sample well from the top and light is emitted from the top and directed to a light detector;
excitation light is introduced into the sample well from the bottom and light emitted from the bottom is directed to a light detector;
light is introduced through the bottom of the well and light which is not absorbed leaves through the top and is directed to a light detector;
no light is introduced to the sample well and light generated by chemical reaction leaves through the top of the well and is directed to a light detector.

Multiple excitation light sources can be included. Two types of excitation light sources are used in a preferred embodiment—a flash light source e.g. a flash Xenon arc lamp, and a continuous wave light source e.g. a quartz tungsten halogen lamp. The light from each source is filtered to provide the desired spectral band for the intended analysis and thereafter the filtered light is shaped and directed to a sample well.

Excitation light is directed via optical fiber channels to enter a sample containing well through either the top via a read head or to the bottom, depending on the optical fiber channel which is selected.

One of several types of optical devices is switched into position to direct light as required for the type of analysis to be carried out. In a preferred embodiment, three types are used, namely, reflective mirrors, dichroic mirrors, and beam splitters, either thin-film beam splitters or partly silvered mirrors Alternatively, they are not used when it is unnecessary to direct the light, e.g. in measuring luminescence and absorbance. A beam dump (an absorber) is provided for use in conjunction with a dichroic mirror or a beam splitter in order to remove excitation light which is not reflected into a sample well and would adversely affect the light detector.

Apertures of various sizes are provided for the excitation light and the emitted light. The selected aperture can be moved into position easily since they are mounted on a moveable plate containing the number of apertures needed for the types of analysis being carried out.

When analyzing a sample by polarization fluorescence, polarizing filters are provided, which filter both the excitation and emitted light either parallel or perpendicular to the polarization direction of the light. In one embodiment, a liquid crystal polarization rotator-linear polarizer combination is used to make it possible to alternate the polarization of the light electronically.

The light emitted by a sample, enters the light detector via a light pipe, i.e. a solid glass pipe, rather than via a lens or multiple group of lenses since imaging of the sample well, or a portion of the sample well is not required.

Light emitted from a sample well may be directed to the light detector from either the top or bottom of the well.

The optical elements are arranged to provide that the excitation light (except for absorbance measurements) has a cross-section equal to the cross-section of the sample well, rather than being limited to a small region within the sample well. Absorbance measurements are made by providing a narrow beam of excitation light at the center line of the sample well. The light emitted from the sample well is not significantly refracted (spread) by the lenses adjacent to the sample well since the emitted light is at the center line of the lenses and collimated.

All measurements of emitted light are made with a single detector in a read head which includes all of the optical elements.

For analysis by absorbance, a diffuser is provided to remove the random polarization caused by excitation light passing through the transparent bottom of a sample well, thus providing more consistent measurements of the emitted light.

The read head remains in one position, while the microplates are positioned horizontally and vertically to accommodate the type of microplate being used.

In one aspect, the invention includes the universal microplate analyzer as configured for analyses by fluorescence, including time-resolved and polarization fluorescence, absorbance, and luminescence.

In another aspect, the analyzer of the invention also includes facilities for carrying out a Luminescent Oxygen Channeling Immunoassay (LOCI), such facilities being designated "Alpha Screen" by the Packard Instrument Company and described in U.S. patent application Ser. No. 09/512,707 and incorporated herein by reference.

DESCRIPTION OF THE PREFERRED EMBODIMENTS OF THE INVENTION

Fluorescence, Absorbance, and Luminescence

Figure 1:
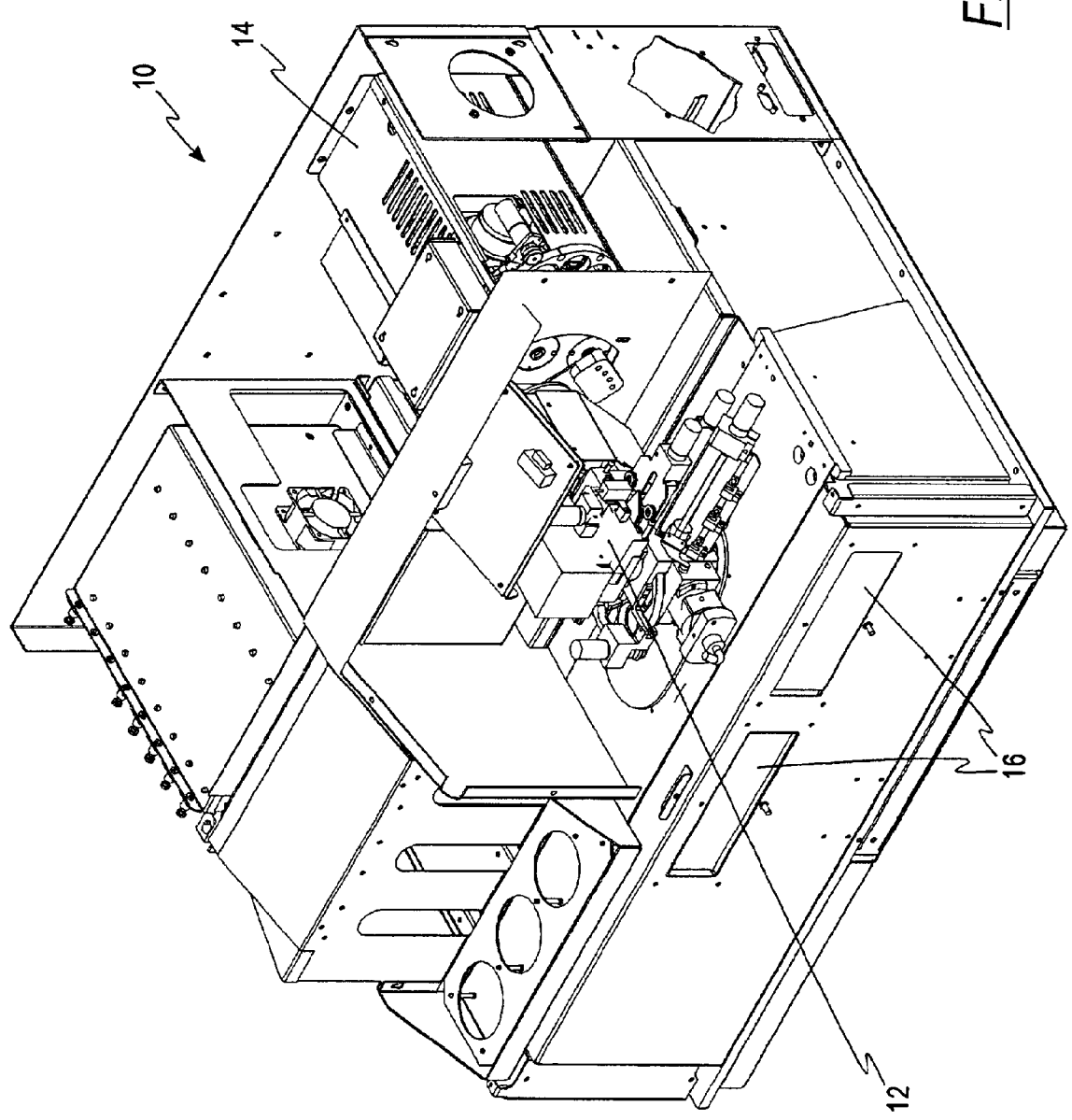
FIG. 1 is a perspective view of one embodiment of the microplate analyzer partly cut away to show internal features.

The analyzer of the invention is used to determine the response of a sample (typically a liquid) to introduction of reagents which react with the sample to provide a measure of certain molecules in the sample. Such samples are often biological samples and when reagents are added, they may emit light with or without being activated by an external source of light (excitation light).

In general, excitation light will be limited to a certain range of wavelengths suitable for the sample being analyzed, while the sample will emit light having a spectral band characteristic of the sample which differs from the light used to excite the response. In other instances, the sample will emit light without use of an excitation light, but in response to reagents which have been added. The emitted light is detected, typically by a photo multiplier tube (PMT), and the quantity of light is used to characterize the sample. In the multi-functional analyzer of the invention, several types of analysis are possible.

In the simplest type of analysis, a sample is contacted with reagents which cause the sample to emit light (Luminescence). No excitation light is required. The light passes through an appropriate optical system and then is measured by the detector.

In another type of analysis, the amount of excitation light supplied to sample well from the bottom passes through an optical system, is measured and compared with the amount of light emitted when a sample is present in the well to provide a measure of the light absorbed by the sample and well (Absorbance).

Fluorescence involves measurement of emitted light from a sample which has been excited by a source of polarized or non-polarized light. Usually, the wavelengths characteristic of the emitted light will be different from that of the excitation light. In one type of analysis (Polarization Fluorescence) polarizing filters are used with both the excitation and emitted light. It is possible to carry out related fluorescence measurements which indicate the mobility of molecules in the samples by the degree to which polarization of the light has been changed by the sample.

In addition to three principal types of analysis just described, facilities may be included to carry out Luminescent Oxygen Channeling Immunoassay (LOCI), such facilities being designated "Alpha Screen" by the Packard Instrument Company.

FIG. 8 schematically illustrates the four principal modes of the analyzer, omitting most of the optical elements, which will be described in more detail below. FIGS. 8a and 8b represent measurement of fluorescence of a sample resulting from excitation light. FIG. 8c represents measurement of absorbance of light passed through a sample. FIG. 8d represents measurement of luminescence. FIG. 8a shows the method of operation in which light is directed into a sample from the top of the well 42, entering via optical fiber channel 34a and being reflected from either a dichroic mirror 22a or a beam splitter 22b into the sample. The emitted light passes through the beam splitter 22b or the dichroic mirror 22a to reach the light detector 18. A beam dump 58 (a light absorber) is positioned to remove the light passing through the beam splitter 22b or dichroic mirror 22a in order to prevent that light from interferring with the emitted light which is going into the light detector 18. FIG. 8b shows the analyzer of the invention operating with samples which are excited by light entering from the bottom of the well via optical fiber channel 34c and which emit light also through the bottom of the well 42 via optical fiber channel 60, which is directed to the light detector 18 via the angled mirror 22c. FIG. 8c shows the alternative operation in which the absorbance of samples is measured. Light enters from the bottom of the sample well 42 from optical fiber channel 34b, passes through the sample and exits from the top of the sample well 42, and proceeds upward to the light detector 18. FIG. 8d illustrates the use of the analyzer of the invention with a sample which is activated by reagents rather than exciting light source (e.g., luminescence). No excitation light is introduced and light emitted by the sample passes upward to the light detector.

External Appearance of the Analyzer

Figure 2:
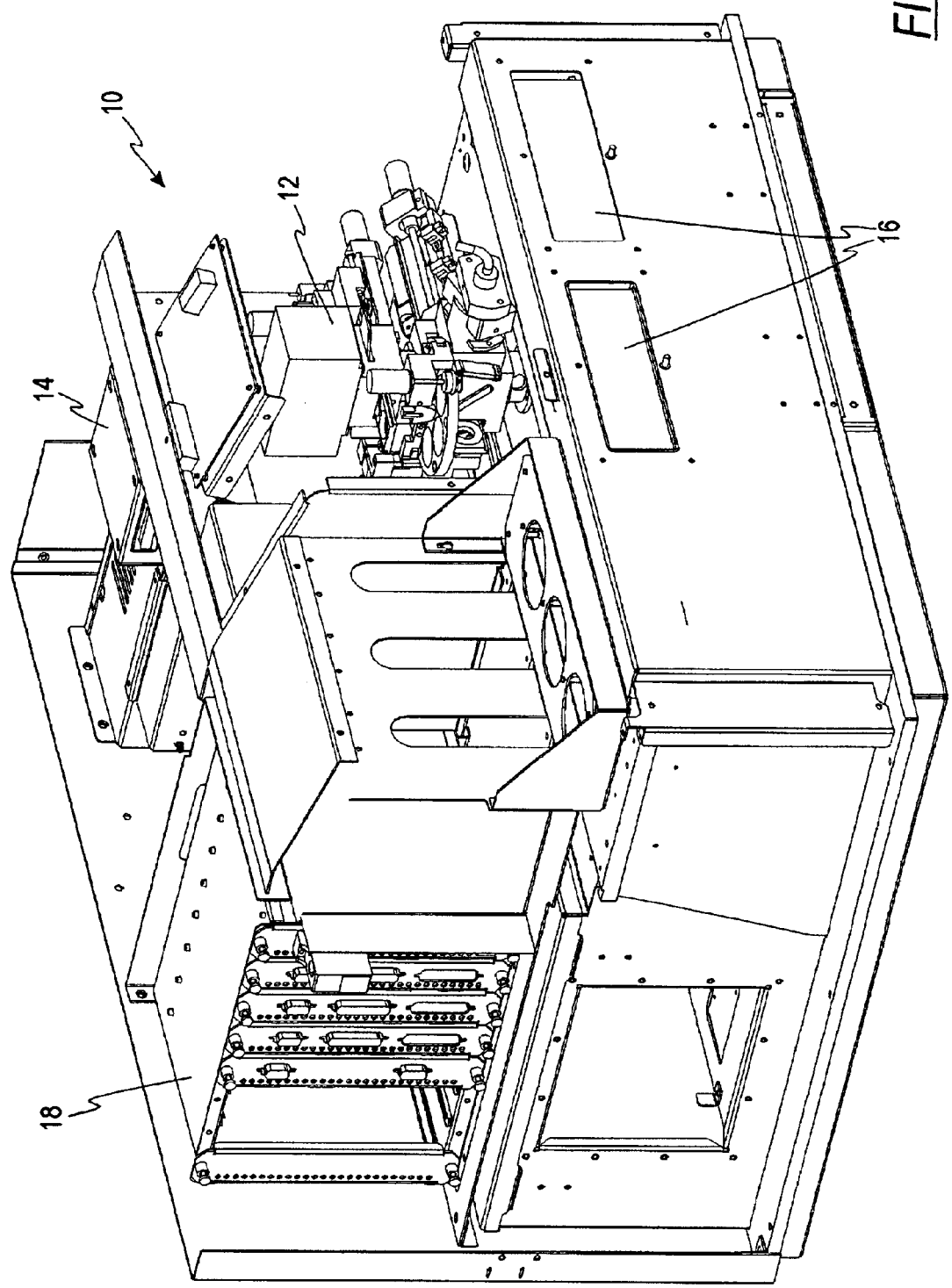
FIG. 2 is a second perspective view of the analyzer of FIG. 1.
Figure 3:
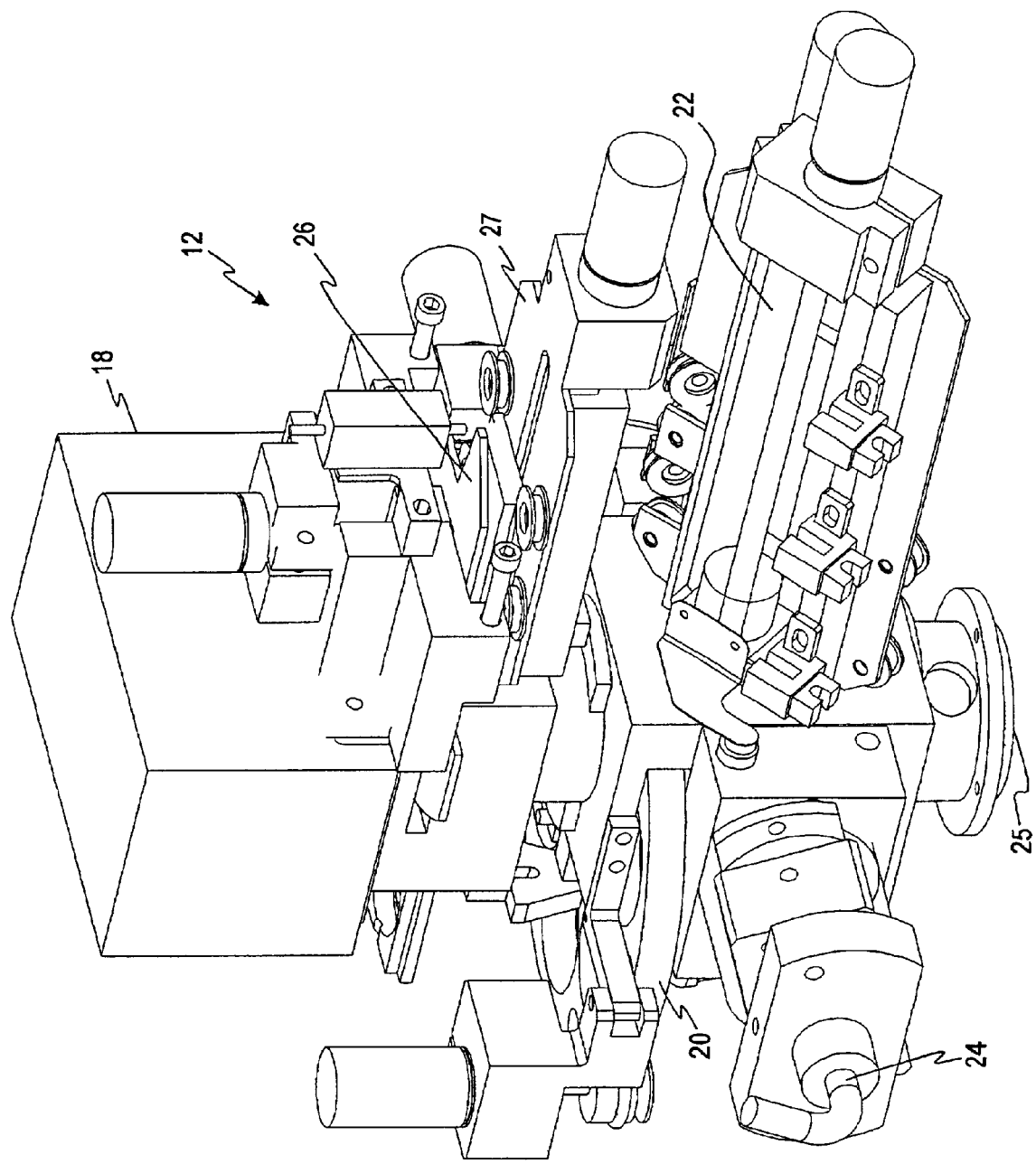
FIG. 3 is a perspective view of the read head of the analyzer of FIG. 1.

In FIGS. 1–6 one embodiment of the analyzer of the invention is illustrated. A second embodiment is similar and modifications will be noted in the description and certain of them are illustrated in FIGS. 3a and 4a.

FIG. 1 provides an overall view of one embodiment of the analyzer 10 of the invention. It is possible to see the read head 12, the illumination module 14 and the ports 16 for insertion of the sample plates.

FIG. 2 shows the cutaway view of FIG. 1 from a different angle, from which the read head 12, the illumination module 14 and sample plate ports 16 are visible. The electronic controls 18 can also be seen. FIG. 3 provides an enlarged view of the read head 12 of the analyzer 10, which includes the light detector 18 (typically a photomultiplier tube), the filter wheel 20 for providing the light detector 18 with the desired spectral band of the emitted light, the optical switching device 22 for introducing the required optical element (i.e., beam splitter, dichroic mirror or reflective mirror), the connection 24 for the fiber channel carrying emitted light from below the sample well, the aperture selector 26, and the polarizer slide for emitted light 27 (used only for polarization fluorescence analysis). In an alternative embodiment, the polarizer slide 27 is omitted and a combined polarizer and filter is mounted in filter wheel 20, which in other embodiments included only a band-pass filter. The microplate being analyzed will be positioned below flange 25.

Figure 3A:
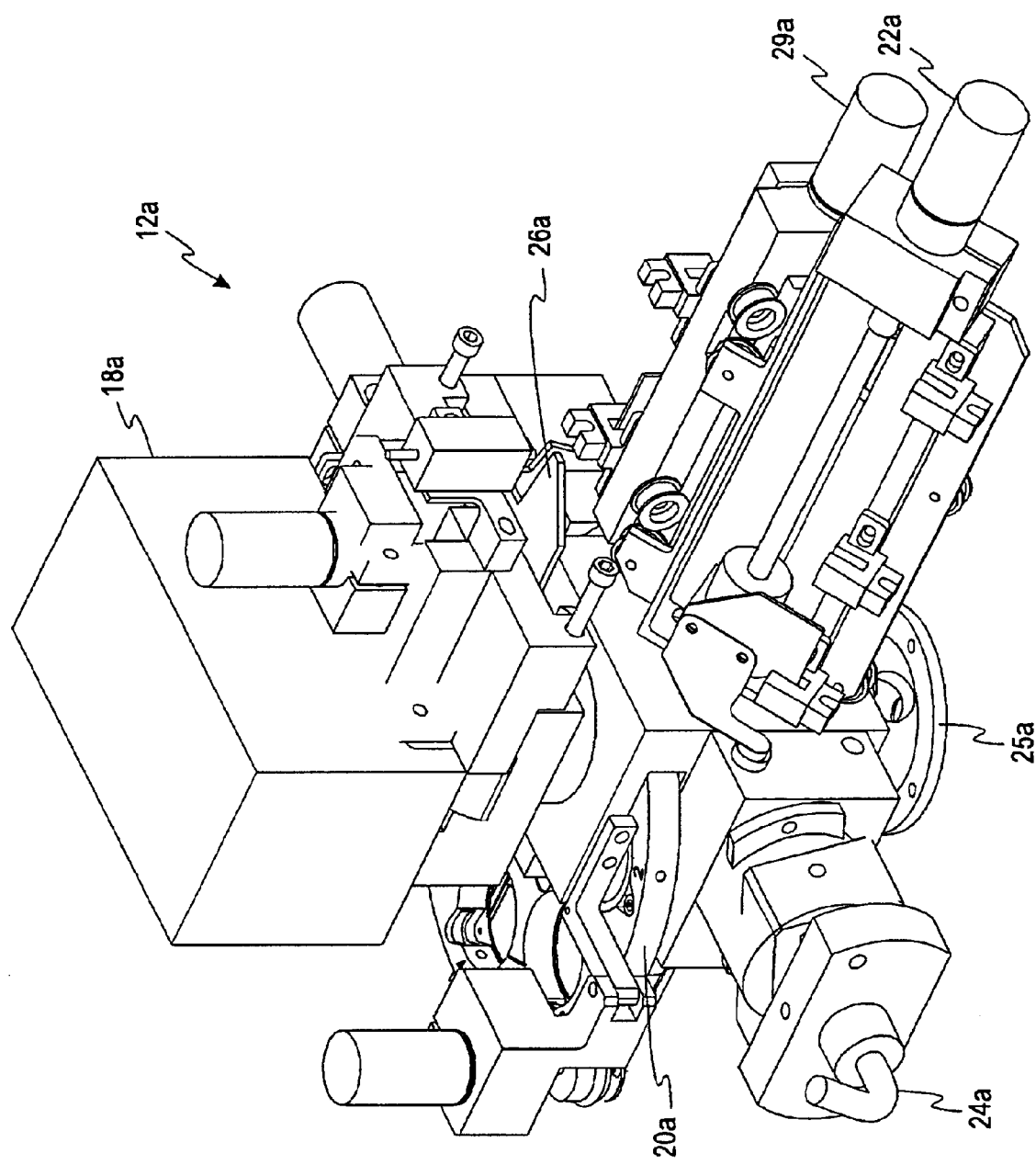
FIG. 3a is a perspective view of the read head of the second embodiment of the analyzer.

FIG. 3a is similar to FIG. 3, but it shows a second embodiment of the analyzer of the invention. The polarizers for the emitted light shown as mounted in slide 27 in FIG. 3 have been omitted, since only one polarizing filter is used and it is mounted in filter wheel 20a. Alternatively, a liquid crystal polarization rotator-filter set could be mounted in filter wheel 20a.

Figure 4:
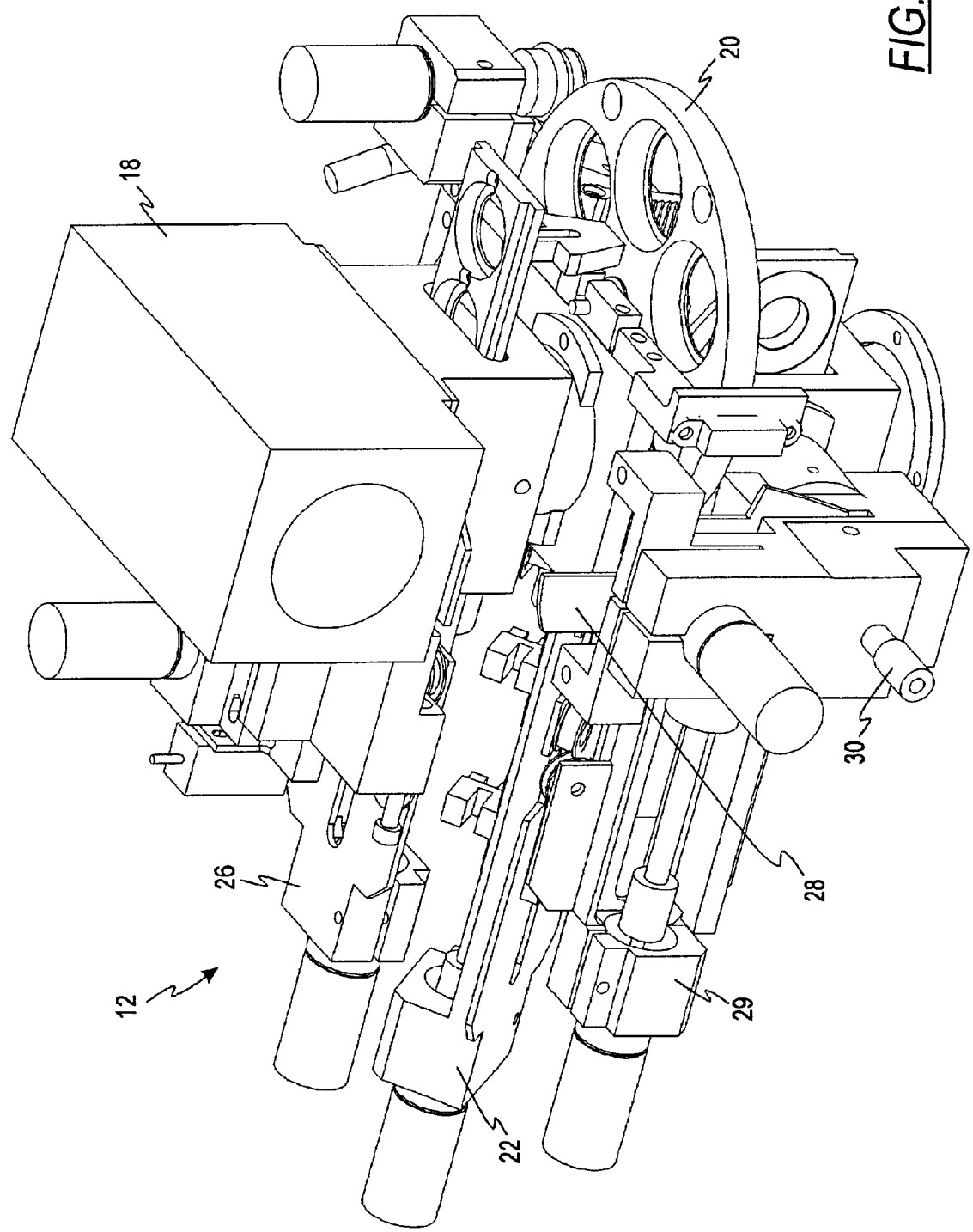
FIG. 4 is a second perspective view of the read head of the analyzer of FIG. 1.
Figure 4A:
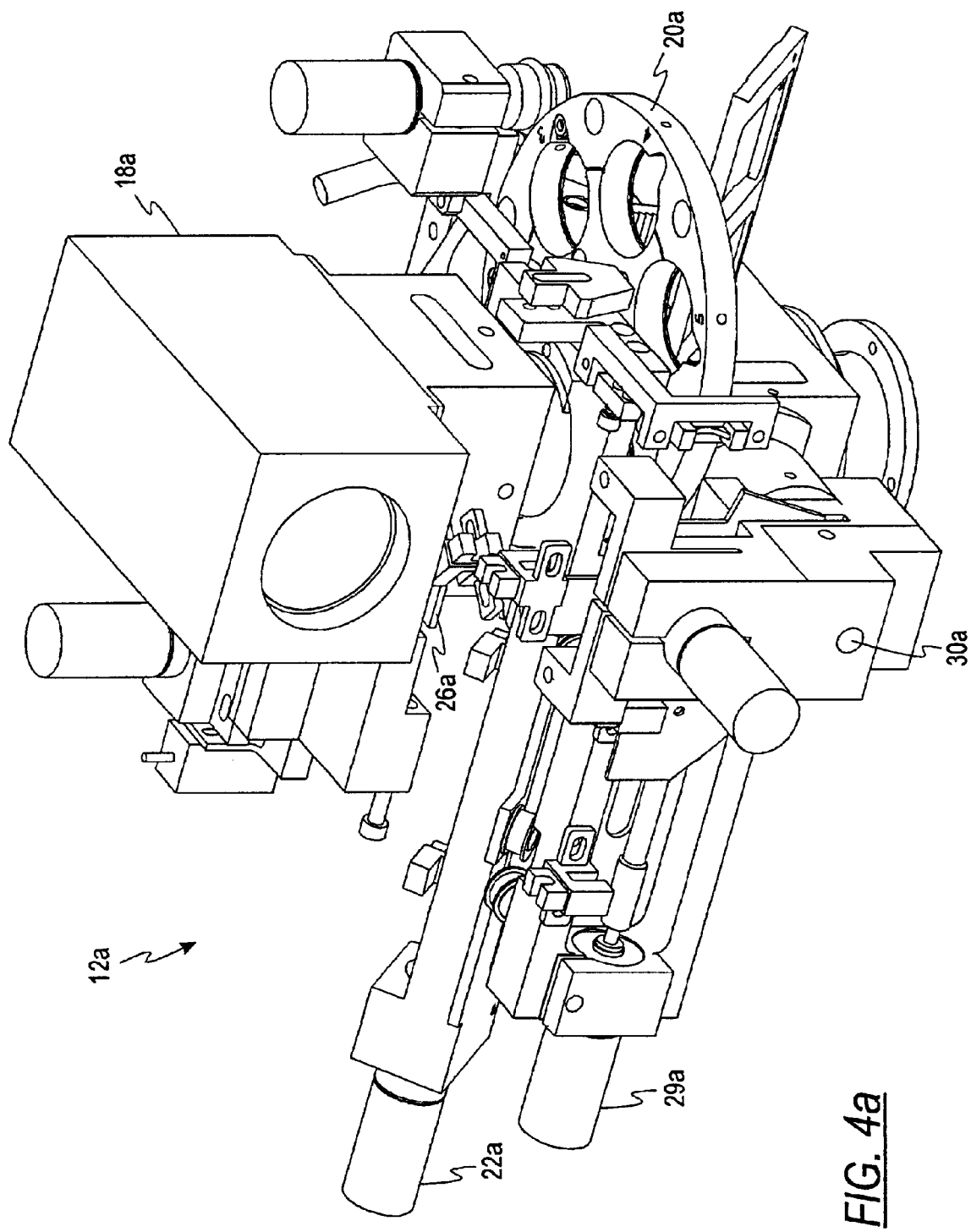
FIG. 4a is a second perspective view of the read head of the second embodiment of the analyzer.

FIG. 4 shows the read head 12 of the analyzer 10 from a different direction, from which in addition to the light detector 18, the filter wheel for the emitted light 20, the aperture selectors 26 and 28, the polarizer slide for excitation light 29, and the optical switching device 22, there can be seen the fiber channel connection 30 for excitation light directed to the top of the sample well. In an alternative embodiment, the polarizer slide 29 includes a liquid crystal polarization rotator in combination with a polarizer of fixed orientation so that the polarization of the excitation light can be varied electronically.

FIG. 4a is similar to FIG. 4, but as in FIG. 3a the slide 27, which mounted polarizers for emitted light in FIGS. 3 and 4 has been omitted. Instead, a polarizing filter is mounted in filter wheel 20a. The polarizing filter is used in combination with the liquid crystal rotator-polarizing filter set for orientation of the excitation light and mounted in slide 29a for fluorescence polarization measurements.

Figure 5:
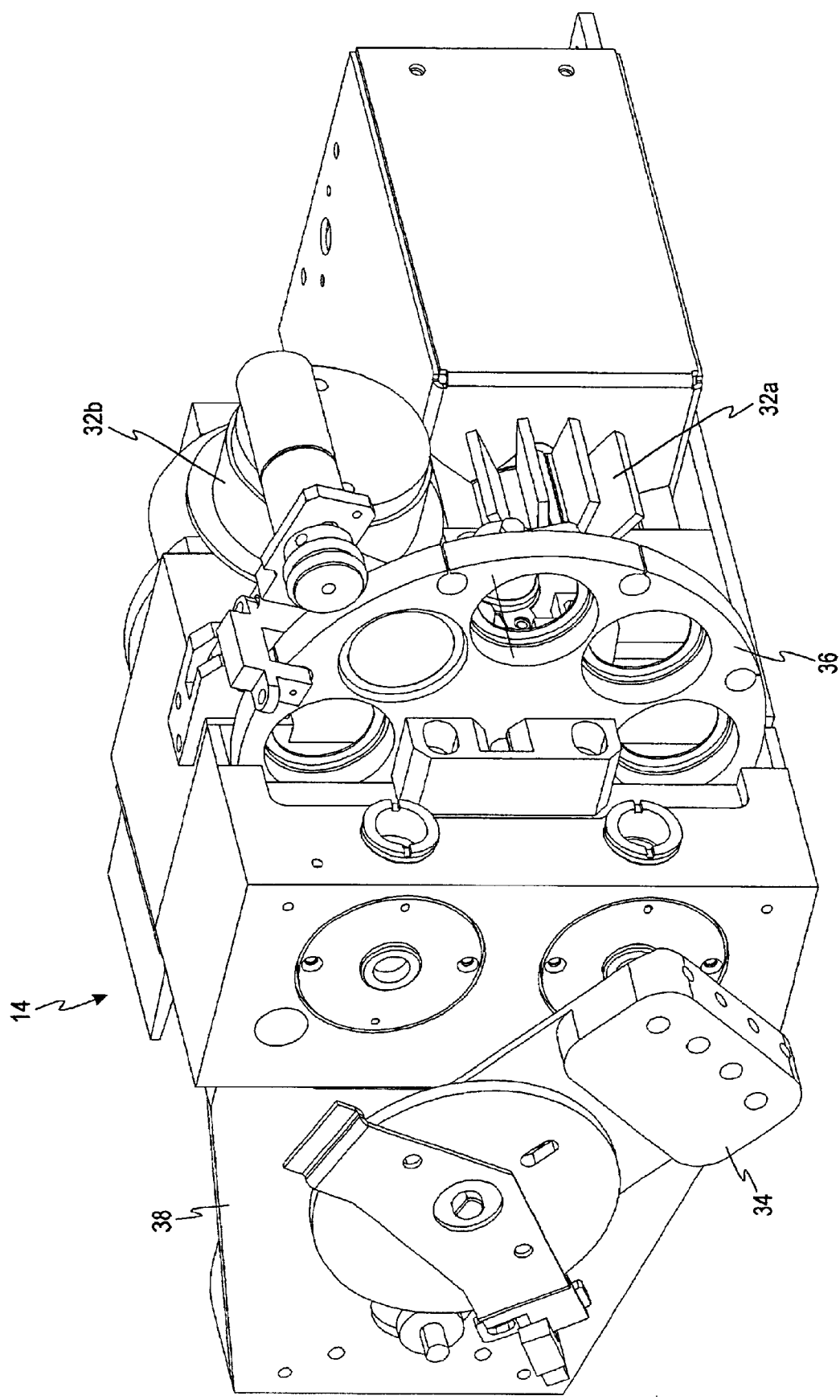
FIG. 5 is a perspective view of the illumination module of one embodiment of the analyzer.

FIG. 5 shows the illumination module 14 which provides excitation light, preferably from a flash Xenon lamp 32a or from a continuous quartz halogen lamp 32b. A filter wheel 36 provides the bandwidth desired for the excitation light. Depending on the type of analysis being carried out, a stepper motor 38 will position one of four possible optical fiber channels connected at 34 so that the light can be transmitted to the proper location, either to the read head, or to below the microplate well.

Figure 6:
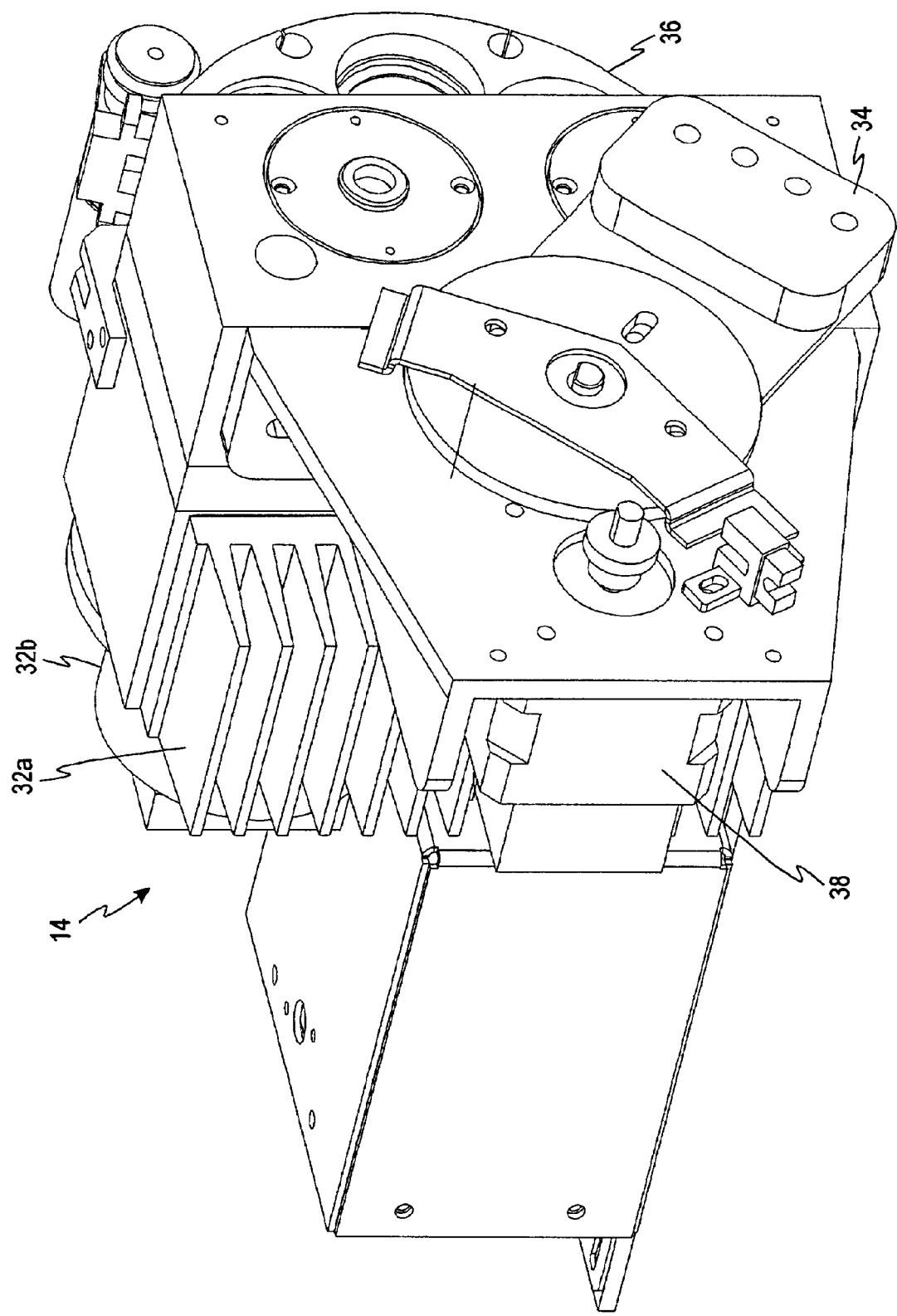
FIG. 6 is a second perspective view of the illumination module of FIG. 5.

FIG. 6 illustrates the illumination module 14 from a different direction. Again the set of connections 34 for the optical fiber channels can be seen. Also the quartz lamp 32b and the flash Xenon lamp 32a light sources. The filter wheel 36 allows the excitation light to be limited to the desired band width for the analysis to be carried out.

Interior Arrangement of the Analyzer

Figure 7:
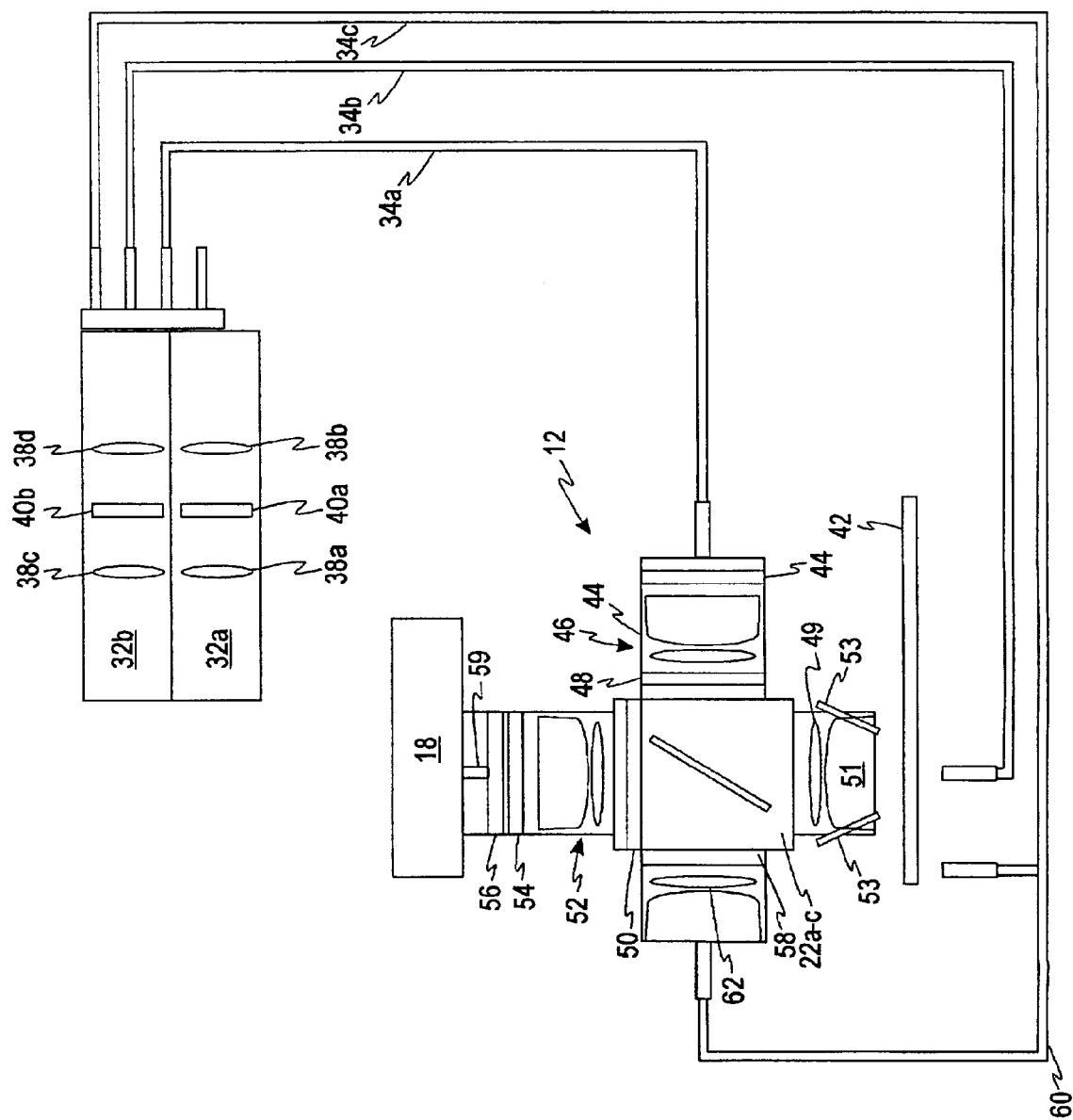
FIG. 7 is a schematic diagram of one embodiment of the analyzer of the invention.
Figure 7A:
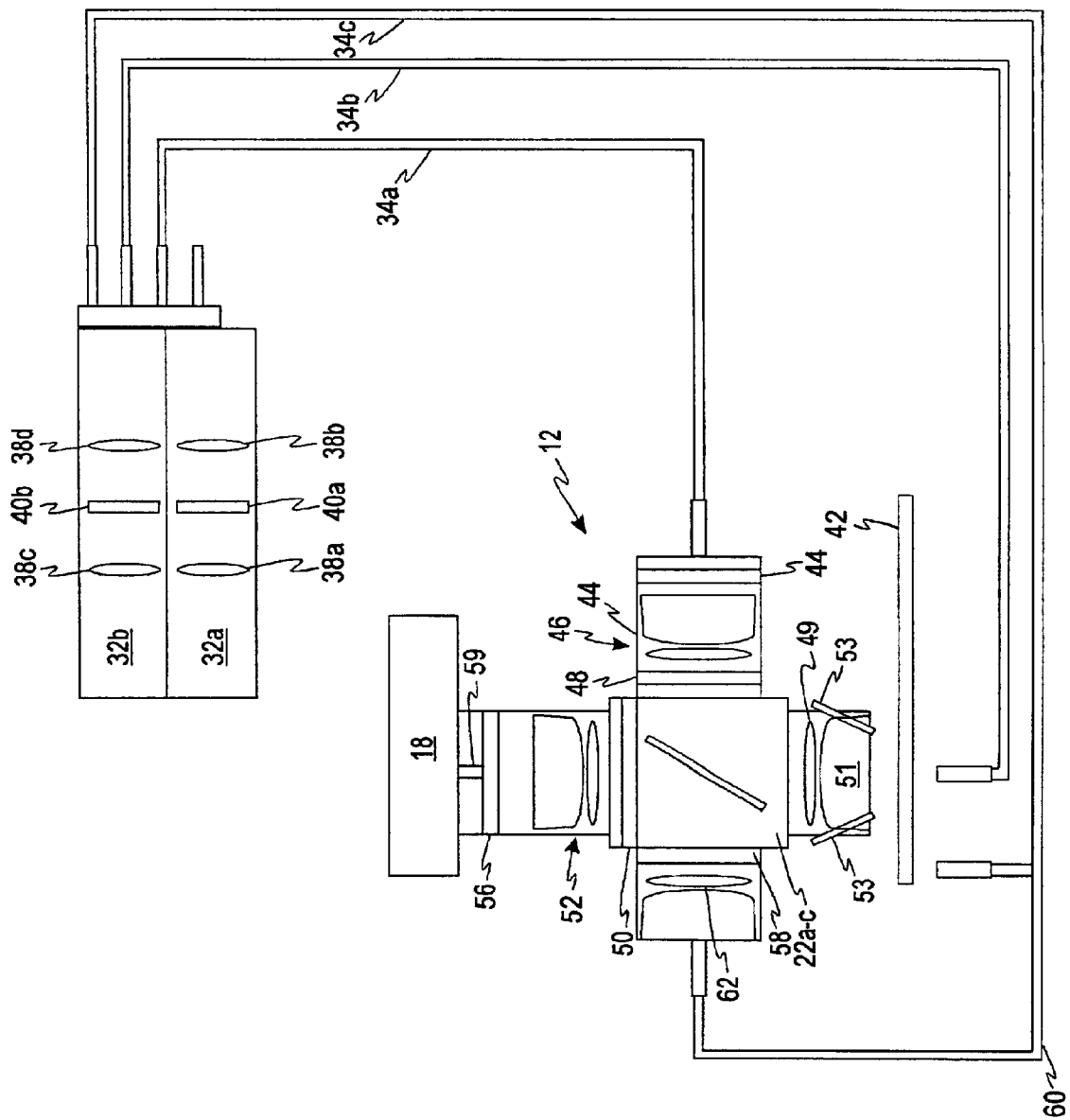
FIG. 7a is a schematic diagram of a second embodiment of the analyzer of the invention.
Figure 8A:
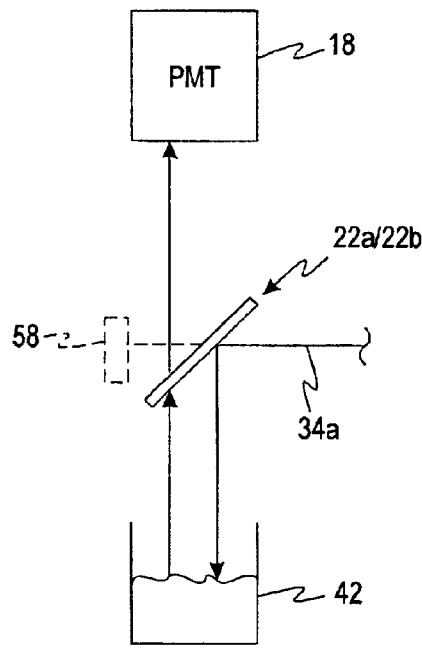
FIGS. 8a–d illustrate four possible modes of operation of the analyzer.
Figure 8B:
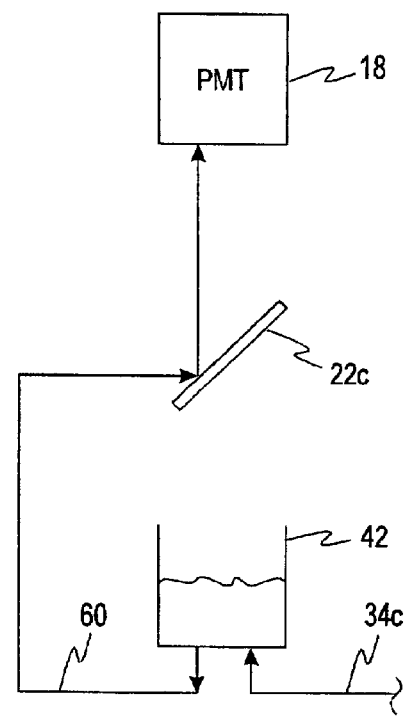
Figure 8C:
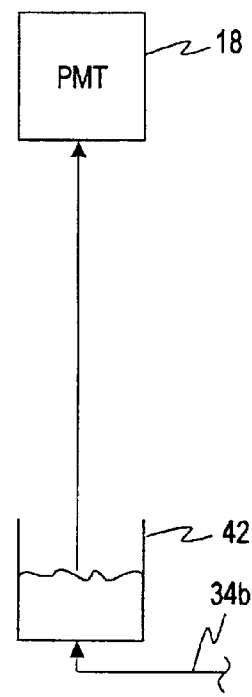
Figure 8D:
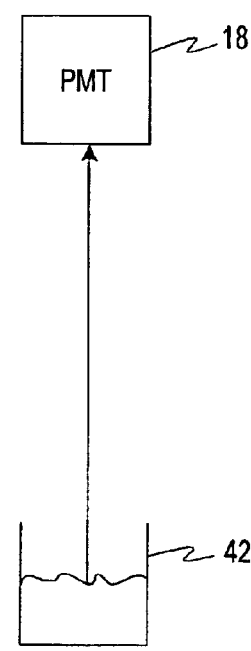

Now, having viewed the instrument from the outside, FIGS. 7 and 7a illustrate schematically how the elements of the analyzer 10 are arranged. The two light sources, preferably a flash lamp 32a e.g. a Xenon lamp and a continuous incandescent lamp 32b, e.g. a quartz tungsten halogen lamp, provide light which is transferred either to the read head 12 or to the bottom of the microplate 42 by one of three optical fiber channels 34a–c. Before entering the light carrying fiber channels 34, the light is shaped and filtered by the lens sets 38a, b, or c, d and bandpass filters 40a or b as shown. It will be recalled that in FIG. 6 a set of filters is mounted in a disk 36 may serve both lamps and can be rotated to provide the spectral band needed for the analysis to be carried out. With a Xenon lamp the filter will usually limit the light to be transmitted to the sample to within a selected narrow bandwidth in the range of 240 to 900 nm, while when a quartz halogen lamp is in use, the filter will usually limit the light to within a selected narrow bandwidth in the range of 340 to 900 nm. The filters used will be familiar to those skilled in the art. They typically are made by vacuum deposition of multiple thin layers of different materials and thicknesses and are commercially available in various spectral bands. The final lens set 38b and 38d will direct the filtered light on the fiber channel selected. The optical fiber channels 34a–c are not necessarily identical. They are chosen for their ability to provide the sample being analyzed with a beam of light most suitable for the type of analysis being carried out. For example, optical fiber channel 34a used for fluorescence measurements will typically be a bundle of fibers, while for absorbance measurements a monofilament 34b would be selected in order to provide a better defined beam of light to the sample.

In FIGS. 5, 6, 7, and 7a of the four possible positions for optical fiber channels 34a–c, only three are shown being used for fluorescence and absorbance measurements. The fourth position provides for future expansion of the analyzer's capacity, such as for example, adding facilities for varying the band width of excitation light provided to a sample by using a monochrometer.

The light transmitted to the sample well in microplate 42 will enter from either the top or the bottom, depending on the type of analysis being carried out. The analyzer of the invention makes it possible to carry out several types of analysis, including fluorescence (including time-resolved and polarization fluorescence), absorbance and luminescence. For certain types of analysis, including fluorescence, the light is introduced into the read head 12 via optical fiber channel 34a through the side, where it passes through one of three available apertures 44 (in 28) and then is collimated by lens set 46 and in polarization fluorescence analysis the light is also polarized through one of two available polarizers 48 (in slide 29), before being passed into the top of the sample well in microplate 42 through additional lens 49 and 51. In an alternative embodiment, a liquid crystal polarization rotator is employed in combination with a fixed polarizer at 48 so that the polarization of the light can be varied electronically. Since the excitation light is intended to extend to the full width of the sample well, apertures 44 are not located adjacent the end of the optical fiber channel 34a, but spaced away from it. The lens set is located at a distance from the optical fiber channel greater than would place the focus point of the lens set at the end of the optical fiber channel. With this arrangement of the aperture and the lens set the light beam widens, rather than being confined to a small region of the sample.

Two types of reflecting mirrors are provided by the analyzer of the invention. In the first type, the excitation light is reflected from a dichroic mirror 22a (one of the possible selections of the optical switch 22), into the desired sample well in microplate 42, where it excites a response which depends on the nature of the sample. The emitted light from the sample has a different characteristic spectral band than that of the excitation light and it passes through the dichroic mirror 22a (that is, not reflected as was the excitation light) to the light detector 18, e.g. a photo multiplier tube. Before reaching the light detector 18, the emitted light passes through one of a set of filters 50 to limit the band width, a lens set 52, if required a polarizer plate 54 (one of two available), an aperture 56 (one selected from four available) and light pipe 59. The detector 18 determines the amount of light received and computation is made by electronic circuits (not shown) of the property of the sample which correlates with the light emitted.

In the second alternative, the light encounters a beam splitter 22b (either a thin-film beam splitter or a partly silvered mirror) which has been moved into position by the optical switch 22. The beam splitter 22b does not selectively pass light above a predetermined wavelength cutoff as does dichroic mirror 22a, but passes all wavelengths. A portion of the light passes through the beam splitter 22b, and is absorbed by the beam dump 58 positioned opposite the light entry point. The remaining light is reflected into the sample from the top of the well in microplate 42. As before, the emitted light passes through the beam splitter 22b in part and is directed to the light detector 18 via filter 50, lens set 52, polarizer plate 56 (if required), aperture 56, and light pipe 59 as previously described. While the beam splitter is not as efficient in directing light as a dichroic mirror, it has the advantage of providing flexibility that the dichroic mirror does not. That is, the beam splitter is capable of handling a wide range of light wavelengths, while the dichroic mirrors are limited to reflecting or transmitting light only below or above a predetermined wavelength.

Two types of beam splitters may be used. One type, a thin-film beam splitter, is made in a similar manner to a dichroic mirror. However, instead of reflecting light below a certain wavelength and passing light above that wavelength, a fraction of all the light is reflected, while the remainder passes through the beam splitter. A second type of beam splitter is a partially silvered mirror which also reflects a portion of the light, depending on the fraction of the surface which has been silvered. In one embodiment of the present invention the beam splitter employs a single elliptically-shaped silvered area in the center of a rectangular piece of glass, thereby making it possible to direct a narrow beam of light into a sample well, while the emitted light passed through the annular clear area around the reflective spot.

In a third method of operation, light is transmitted through one of the optical fiber channels 34c to the bottom of the sample well in microplate 42, where it passes into the sample and excites a response from the sample having a different wave length. The emitted light exits the well in sample plate 42 through the bottom and is transmitted via another optical fiber channel 60 to a side of the read head 12 opposite that through which excitation light was introduced. The emitted light is collimated by a lens set 62 and then is reflected upward into the light detector 18. In this method, a reflective mirror 22c is placed in position by the optical switch to reflect all of the light emitted from the sample. The reflected light passes through the emission filter 50, the lens set 52, aperture set 56 and the light pipe 59, before reaching the light detector 18.

A fourth method of operation involves the introduction of light into a sample from the bottom of the well in microplate 42 via optical fiber channel 34b. The objective is to determine the amount of light absorbed, rather than the amount of emitted light. In this mode, all of the means used in the other three methods, i.e. the reflective mirror 22c, the dichroic mirror 22a, and the beam splitter 22b are moved out of the light path by the optical switch 22 so that the light which passes through the sample 42 is directed upwardly into the light detector 18 following the path previously described. A diffuser is used with filter 50 to remove polarizing effects of the sample well, since the excitation light entering the sample well is randomly polarized by the transparent bottom of the well and varying from well to well. To avoid affecting the measurement made by the detector 18 the diffuser is used in this mode of analysis.

It is also possible to use the analyzer of the invention to make measurements of the luminescence of samples, that is samples which do not require light excitation. In such instances, when reagents are mixed with the sample (e.g. via injectors located in slots 53 in the lens just above the sample well), light is emitted by the sample. Light will be passed upwardly, usually without contacting any of the light diversion means described above (i.e., the optical switch 22), into the light detector 18 via filter 50, lens 52, aperture 56, and light pipe 59 for measurement of the amount of light emitted by the sample (polarizing filter 54 is not required). Alternatively, a dichroic mirror may be positioned in the emitted light path if desired since it will pass most of the light in the visible range.

FIG. 7a corresponds to the schematic drawing shown in FIG. 7, except that the optical system acting on the excitation light and the emitted light has been revised. As before, two light sources, e.g. Xenon lamp 32a and quartz lamp 32b, provide light which is passed to the read head 12 or to the bottom of a microplate 42 by one of three optical fiber channels 34a–c. Before entering the light carrying fiber channels, the light is shaped and filtered by the lens sets 38a–c and b–d and filters 40a–b.

As before, when light is directed into the top of a sample well either a dichroic mirror or a beam splitter is used to direct the excitation light and the emitted light. Both are capable of directing light, but they affect the light differently. A dichroic mirror is able to pass light above a predetermined wave length, but will reflect passage of light having shorter wave lengths. Thus, the excitation light is reflected into the sample well, while the emitted light, having a longer wave length band width than the excitation light, is able to pass through the dichroic mirror enroute to the detector. The term "beam splitter" could be interpreted as including a dichroic mirror also, but as used here, a beam splitter is either a partially silvered mirror or a thin-film beam splitter. In both types, light of the entire light spectrum is either passed or diverted. Part of the light is reflected and part passes through the beam splitter. Either type of beam splitter could be used. If a partially silvered mirror is used, it is preferred that a rectangular piece of glass having an oval-shaped silvered central spot is used to direct a narrow beam of excitation light into the sample well. When the emitted light from the sample well reaches the partially silvered mirror, the portion of the emitted light which is not reflected away from the central mirrored spot passes through the clear portion of the beam splitter to the photomultiplier tube.

While the analyzer of FIG. 7a operates in a closely related manner to that of the analyzer shown in FIG. 7, there is an important difference in the manner in which polarized light is used to analyze samples by polarization fluorescence, which is able to assess the mobility of molecules in the sample-well. A polarizer filter is used to limit the excitation light to linear polarization in one direction. When the linearly polarized excitation light strikes a sample in the well, the sample fluoresces and emits light which is not fully polarized in the same direction, thus providing an indication of the mobility of the molecules in the sample. This difference in light polarization is determined by the reading of the emitted light by the photomultiplier tube.

In the analyzer of FIG. 7, polarizing filters (48) are changed to provide excitation light polarized first in one direction and then in a direction perpendicular to the first direction. In the optical system shown in FIG. 7a, the excitation light is polarized by a linear polarizer attached to the front of a liquid crystal polarization rotator. The linear polarizer filters the excitation light such that the light leaving the polarizer is substantially completely linearly polarized. With no voltage applied to the liquid crystal polarizer, it is a passive device and the linearly polarized light passes on to the sample well. When voltage is applied to the liquid crystal rotator, the device is active and the linearly polarized light that leaves the liquid crystal rotator is oriented perpendicularly to the linear polarized light resulting from the passive state of the rotator.

In both FIGS. 7 and 7a the linearly polarized excitation light strikes the sample, causing the sample to fluoresce. Depending on the nature of the sample, the light emitted by the sample can be polarized, de-polarized, or a combination of the two. This emitted light is collected by the read head optics and passed through a linear polarizer placed on the front of an emission band-pass filter before reaching the photomultiplier tube (FIG. 7a) or in slide 54 in FIG. 7. Since the linear polarizer only can pass light having the same orientation, the characteristic orientation of the light emitted from the sample will determine how much light reaches the photomultiplier tube. If the excitation light polarizer and the emitted light polarizer are parallel, then all the light from the sample having that light orientation will reach the detector tube. If the excitation light polarizer and the emitted light polarizer are perpendicular, then the only light which reaches the detector tube is that which has been changed by excitation of the sample. Thus, if the sample has not re-oriented the light and the polarizers are parallel, the amount of light reaching the detector tube is proportional to the amount of the polarized excitation light. On the other hand, if the polarizers are perpendicular, the amount of emitted light reaching the detector tube is cancelled. However, if the orientation of the light emitted from the sample has been changed, the polarizer acting on the emitted light will only pass that portion which retains the original orientation of the excitation light or which has the orientation of the emission polarizer. The difference between measurements made with the polarizers in parallel compared with those made with the polarizers in perpendicular indicates the degree of mobility of the molecules in the sample.

In an analyzer having a liquid crystal polarization rotator-polarizer set, the excitation light can be changed electronically so that the polarization of the light is either parallel or perpendicular to the polarization of the emission polarizer. FIG. 7a shows an analyzer in which the excitation light is passed through a liquid crystal polarizer, while the emitted light is passed through a polarizer having a single orientation. Of course, the reverse arrangement is equally feasible. That is, the liquid crystal polarizer could be located to act on the emitted light, while a polarizer having a fixed orientation could be used to polarize the excitation light.

In a preferred embodiment, the fixed polarizer is adjacent to a band-width filter placed in a multi-position wheel positioned in the path of the emitted light. Thus, the separate 2-position emission polarization plate 27 shown in FIGS. 3 and 4 of the application may be omitted, as shown in FIGS. 3a and 4a.

Description of the Analyzer in Each Mode of Analysis

Fluorescence measurements can be made in four modes:

Excitation light enters the top of the microplate well and light is emitted from the sample well from the top also.

Excitation light enters the bottom of the microplate well and light is emitted from the sample well and returned by optical fiber channel to the read head.

Time-resolved fluorescence using a flash lamp light source sends the excitation light into the top of the microplate well and light is emitted from the sample well from the top.

Polarization fluorescence sends polarized excitation light into the top of the microplate well and light is emitted from the sample well from the top and is polarized again before reaching the detector.

The analyzer is programmed to place the proper optical elements in position for the selected analysis. In the first type of fluorescence a continuous incandescent lamp supplies excitation light, which is collimated by a first lens and then filtered to provide the desired wavelength range and finally the light is shaped by a second lens to provide an image of the light source to the selected fiber optic channel. The optic fiber channel terminates at one side of the read head, where the beam of light leaving the fiber optic channel is allowed to widen until it reaches an aperture which determines the size of the excitation light beam which will reach the sample well. It is a feature of the analyzer of the invention that, rather than confining the excitation light to a small region within the sample well, that the entire cross-section of the sample well receives the excitation light and emits light from the entire cross-section of the well. Following the aperture, a lens collimates the light and it passes to a partly-reflecting mirror, typically either a thin-film beam splitter or a partly silvered mirror, although use of a dichroic mirror is not excluded. The portion of the excitation light which is reflected 90 degrees toward the sample well then passes through two lenses before entering the sample well and the sample which had been placed therein. Since the partly-reflecting mirror passes only a portion of the excitation light to the sample well, the remainder of the light passes through the mirror and meets the beam dump, a feature of the invention. By absorbing the unused excitation light, the beam dump prevents the light from entering the the optical channel leading to the detector and affecting the measurement of the emitted light. The sample in the sample well emits light in response to the excitation light. The emitted light passes through the pair of lenses above the sample well and then through the partly-reflecting mirror and enters the portion of the read head containing optical elements associated with emitted light in all modes of analysis. First, the emitted light is passed through a filter to limit it to the band of light wavelengths to be measured. Then, the filtered light is passed through a lens to focus it, after which the light passes through an aperture to block stray light and enters the light pipe before reaching the detector.

In the second mode of analysis by fluorescence the excitation light from the continuous incandescent lamp is shaped and filtered as described above, but a separate optical fiber channel is used to direct the light to the bottom of the sample well. The light beam exiting the optical fiber channel widens to fill the cross-section of the sample well. Light emitted from the sample in response to the excitation light is received by the same optical fiber channel and transferred to the side of the read head located opposite to the entry port for the fiber optic channel discussed above which supplies excitation light to the top of the sample well. The emitted light passes through a lens to widen the light beam and then it is reflected by a fully-silvered mirror 90 degrees into the emitted light optics. The emitted light is passed through a band-pass filter to limit the light band width and then a lens narrows down (or focuses) the light and directs it to the light pipe as described above.

Time-resolved fluoresence uses substantially the same optical elements as those used in the first type of fluoresence described above, except that a flash lamp is used rather than a continuous incandescent lamp. Another difference is that, instead of a partly reflective mirror, a dichroic mirror is used, which is also partly reflective, but which reflects the portion of the light band below a cutoff wavelength value and passes light above that cutoff wavelength. The emitted light from the top of the sample well passes through the pair of lenses and through the dichroic mirror (that is, the portion of the emitted light having wavelengths above the cutoff value). The portion of the emitted light passing through the dichroic mirror then passes through the band-pass filter, the lens and aperture and finally through the light pipe before reaching the detector.

Polarization fluoresence is done using substantially the same optical elements as with the first type of fluoresence described above, except that both the excitation light and the emitted light are polarized as discussed above. The continuous incandescent lamp provides excitation light, which is shaped by a lens, filtered, and then passed through a second lens to provide an image of the lamp to the optical fiber channel. The light passes through the optical fiber channel and enters the read head, where it is allowed to widen and then passed through an aperture. The light is collimated by a lens and then passed through a polarizing filter. As explained above, polarizing filters are used to condition both the excitation and emitted light. During the analysis, the filters pass the light in the same direction at one time and at another time in directions perpendicular to each other. In one embodiment of the analyzer of the invention, filters having fixed orientation are switched into position as required to provide either parallel or perpendicular orientation of the light. In another embodiment, a liquid crystal polarization rotator is combined with a fixed polarizing filter having a simple orientation so that the light orientation can be changed electrically using the liquid crystal polarization rotator. The excitation light and emitted light paths are the same as described for the first type of fluoresence analysis, but, when polarization of the light is desired, the polarizing filters are inserted after the light has passed through a band-pass filter on the excitation path and band-pass filtered after polarization on the emission path.

Analysis by absorbance is carried out with the universal analyzer of the invention in a significantly different sequence of optical elements, but remaining within the general scope of the instrument already described. Either the continuous incandescent lamp or the flash lamp may be used. The excitation light is passed through a first lens, a band width filter and a second lens to form an image of the lamp at the optical fiber channel used for absorbance measurements. A mono-filament is used which terminates at the bottom of the sample well with a collimating lens, so that a very narrow light beam enters and leaves the sample well. The light enters through the bottom of the sample well, as was discussed in connection with one type of fluorescence above. However, the emitted light exits from the top of the sample well, then passes through the pair of lenses positioned immediately above the sample well and through an open space in the slide (optical switch) which contains the mirrors previously discussed, that is, the slide is moved so as to take the mirrors out of the way of the light. The light enters the emission optical section of the analyzer. In absorbence, a diffuser is also provided in order to remove the random polarization which has been found to be caused by the plastic bottom of the sample wells, which exhibit some pseudo-birefringence, that is not consistent among the sample wells. Since some detectors are sensitive to polarization of the light they receive, adding the diffuser improves the accuracy and consistency of the detector's measurements. After the diffuser, the light passes through a lens and is focused, then passes through an aperture and the light pipe to the detector.

Finally, luminescence measurements do not require many of the optical elements needed for the other types of analysis just described. No excitation light is used. Instead, reagents are introduced into the sample well and light emitted by the sample in response to the reaction which has been induced passes through the pair of lenses immediately above the sample well, through the open space in the mirror slide (optical switch) (as discussed in connection with absorbence), or alternatively the dichroic mirror may be used to pass the emitted light to the emission optical section. The emitted light passes through a band-pass filter, a lens to collimate the light, an aperture and finally the light pipe before reaching the detector.

Preferred Construction of the Principal Elements of the Universal Analyzer

Now that the operation of the analyzer has been discussed, the preferred construction of the principal elements will be described.

In the preferred embodiment, excitation light will be provided by either a flash lamp, such as a Xenon arc lamp, or a continuous incandescent lamp, such as a quartz halogen lamp. Alternatively, other light sources such as continuous Xenon, deuterium, laser (gas or solid state), or LED could be substituted. It is also feasible to position the light source outside the analyzer itself and to introduce the excitation light to the analyzer through one or more optical fiber channels.

Filters are used to limit the wavelength range of the excitation and emitted light in order to minimize the effect of light which does not represent the wavelength characteristic of the sample being analyzed. For example, in fluorescence the excitation light would be passed through a filter to remove all light except that within the selected narrow band e.g. 475 to 495 nm. The emitted light would then be filtered to allow only light in the selected narrow band e.g. 520 to 550 nm to reach the detector. The filters are available commercially in predetermined ranges. They are produced by the thin-film technology previously mentioned. Since the analyzer of the invention is able to perform multiple analyses different filters will be needed. They are chosen for the types of analysis anticipated and typically mounted in a slide or wheel which is driven by motor-gear sets under computer control so as to place the desired filter in the path of light for each type of analysis.

Lenses are provided to shape both excitation light and the emitted light. In the illumination module, lenses are used to direct the excitation light to the optical filter channels. When excitation light is directed into a sample well from the top the light is collimated and limited by a suitably sized aperature. Light emitted from the sample also passes through lens sets to collimate and focus the light before it reaches the detector. Design of such lenses is conventional and requires no discussion here.

Multiple apertures are provided in the analyzer in order to define the area to be illuminated and to exclude light reflections which could interfere with the analysis being carried out. Typical apertures will have a cross-sectional area of about 2 $mm^2$ to 24 $mm^2$ (0.003 to 0.037 $in^2$) to provide for sample wells having similar areas. In one embodiment three apertures are mounted in a slide which is moved by a motor-gear set under computer control to place the desired aperture in position. Multiple apertures are also used with the emission light. They will have cross-sectional areas of about 0.85 to 24 mm$^2$ (0.001 to 0.037 in$^2$) and are placed in a multi-position slide positioned just before the light pipe in order to minimize stray light from outside the illuminated area.

The light-pipe is a transparent glass cylinder placed adjacent to the apertures and before the detector to collect and guide emitted light efficiently. No lenses are required and no image is formed at the detector.

Excitation light which is not reflected into the top of a sample well is directed to a beam dump, which is a black anodized aluminum surface shaped to absorb the unwanted light transmitted by the dichroic mirror or beam splitter and thus prevent such light from affecting the detector output. It is moved away by the optical switch through a magnetic connection when the emitted light is read from the bottom of a sample well.

The plano convex lens closest to the top of a sample well contains two narrow slots, typically about 1 mm in width, which permit access to the sample well of injectors to supply reagents used in analysis of a sample. In many instances, one or more reagents are added to the sample well. The response of the sample to the reagents is determined by measuring the light emitted by the sample, both with and without the use of excitation light. Examples of analysis by luminescence and fluorescence include calcium uptake and reporter gene.

The analyzer of the invention can be expanded to include alternative sources of light in the illumination module, multiple read heads, and Alpha Screen facilities, such as are described in pending U.S. patent application Ser. No. 09/512,707, incorporated herein by reference. Additional flexibility, speed, and scope can be had by increasing the number of light sources, read heads, or Alpha Screen facilities. For example, adding an Alpha Screen unit makes it possible to carry out a different type of analysis than those described. Adding multiple facilities makes it possible to increase the speed with which sample plates are analyzed.

As previously mentioned, the filter optic channels can be chosen to provide the light most suitable for the type of analysis being carried out. Generally, factors such as light band width, beam diameter, and aperture size will affect the type of fiber optic channel selected. For example, silica or liquid filled fibers are preferred for UV compatibility.

Typical sample plates contain 6 up to 1536 sample wells. Since the sample plates have a similar overall size, it is clear that the dimensions of the sample wells vary significantly. Also, the spacing of the sample wells differs among the commonly used sample plates and the height of the sample plates varies in the range of 10–25 mm. Consequently, it is necessary to move the sample plate to locate the individual sample wells in the correct position to receive excitation light and/or to emit light from the sample to the detector. The analyzer of the invention provides means for positioning each sample well by a plate carrier with precision motor control in each of the three axes, i.e. horizontal and vertical.

Supplemental Features of the Invention

In addition to the principal features of the universal analyzer of the invention, a number of other features may be included. These include:

Heating and cooling of the microplates to control the temperatures of the samples as required to assure accurate measurements are made.

The multiple optical fiber channels may be moved by a stepper motor into the proper position for selecting the excitation light source and selecting the path of the emitted light, i.e. from the top or bottom of the sample well.

What is claimed is:

1. A universal microplate analyzer comprising:
    (a) an illumination module including:
        (1) as an excitation light source, a continuous wave light source and optionally, a flash light source;
        (2) a means for shaping and filtering the light from said excitation light source;
    (b) multiple optical fiber channels for transmitting the shaped and filtered excitation light to a read head or to the bottom of a microplate well;
    (c) at least one read head including:
        (1) a means for shaping and optionally polarizing the shaped and filtered excitation light received from a first one of said optical fiber channels;
        (2) an optical switch including a minor and beam splitter to reflect the shaped and optionally polarized excitation light to a sample in a microplate well;
        (3) a means for shaping, filtering, and optionally polarizing light emitted by said sample in response to said excitation light directed into said sample; and
        (4) a light detector for measuring the amount of said emitted light received from said means for shaping, filtering, and optionally polarizing light.

2. An analyzer of claim 1, further comprising a second one of said multiple optical fiber channels for transmitting shaped and filtered excitation light to the bottom of a microplate well and a third one of said multiple optical fiber channels for transmitting to said read head the light emitted by a sample in said microplate well from the bottom of said microplate well in response to said shaped and filtered excitation light.

3. An analyzer of claim 2, wherein said read head further comprises:
    (c)(5) a means for shaping said emitted light received from said third optical fiber channel, and
    (c)(6) a reflective mirror further included in said optical switch for directing the shaped emitted light received from said third optical fiber channel to said light detector.

4. An analyzer of claim 1, comprising a fourth one of said multiple optical fiber channels for transmitting excitation light to the bottom of a microplate well and wherein said optical switch includes a means for transmitting light not absorbed by a sample in said microplate well to said light detector.

5. An analyzer of claim 1, wherein a light pipe is disposed between said means for shaping, filtering, and optionally polarizing emitted light and the said light detector.

6. An analyzer of claim 1, wherein said excitation light source is at least one member of the group consisting of a quartz tungsten halogen lamp, a flash Xenon lamp, a continuous Xenon lamp, a deuterium lamp, a laser, and an LED.

7. An analyzer of claim 6, wherein said excitation light source is a quartz tungsten halogen lamp.

8. An analyzer of claim 6, wherein said excitation light source is a Xenon arc lamp.

9. An analyzer of claim 1 for analysis of a sample by fluorescence comprising:

(a) an illumination module including:
 (1) as an excitation light source, a continuous wave light source;
 (2) a means for shaping and filtering the light from said excitation light source;
(b) said first one of said multiple optical fiber channels for transmitting the shaped and filtered excitation light to a read head;
(c) said read head including:
 (1) a means for shaping and optionally polarizing the shaped and filtered excitation light received from said first one of said multiple optical fiber channels;
 (2) a beam splitter or optionally a dichroic mirror for reflecting the shaped and optionally polarized excitation light to the top of a sample in a microplate well;
 (3) a means for shaping, filtering, and optionally polarizing light emitted from said sample from the top of said microplate well; and
 (4) a light detector for measuring the amount of said emitted light after being shaped, filtered, and optionally polarized.

10. An analyzer of claim 9, wherein said means for shaping and filtering the excitation light comprises a first lens for directing the excitation light to a filter, a filter for limiting the excitation to a selected narrow band within the range of 340 to 900 nm, and a second lens for directing the filtered excitation light to said optical fiber channel.

11. An analyzer of claim 9, wherein said means for shaping and optionally polarizing the excitation light received from said optical fiber channel includes an aperture, a lens for shaping said light, and an optional polarizer.

12. An analyzer of claim 11, wherein said means for shaping and optionally polarizing the excitation light received from said optical fiber channel includes an aperture, a lens for shaping said light, and a polarizer.

13. An analyzer of claim 9, wherein said beam splitter is a thin film beam splitter.

14. An analyzer of claim 9, wherein said beam splitter is a partially silvered mirror.

15. An analyzer of claim 9, wherein said beam splitter is rectangular glass and has an oval silvered portion in the center.

16. An analyzer of claim 9, wherein said means for shaping, filtering, and optionally polarizing emitted light includes a filter, a lens, an optional polarizer, an aperture, and a light pipe.

17. An analyzer of claim 9, wherein said means for shaping, filtering, and optionally polarizing emitted light includes a filter-polarizer set, a lens, an aperture, and a light pipe.

18. An analyzer of claim 12, wherein said polarizer comprises a liquid crystal polarization rotator and a fixed polarizer.

19. An analyzer of claim 17, wherein said filter polarizer set comprises a liquid crystal polarization rotator and a fixed polarizer.

20. An analyzer of claim 9, wherein said excitation light source is at least one member of the group consisting of a quartz halogen lamp, a continuous Xenon lamp, a deuterium lamp, a laser, and an LED.

21. An analyzer of claim 20, wherein said excitation light source is a quartz halogen lamp.

22. An analyzer of claim 9, further comprising a beam dump for absorbing excitation light passing through said beam splitter.

23. An analyzer of claim 1 for analysis of a sample by time-resolved fluorescence comprising:

(a) an illumination module including:
 (1) as an excitation light source, a flash light source;
 (2) a means for shaping and filtering the light from said excitation light source;
(b) said first one of said multiple optical fiber channels for transmitting the shaped and filtered excitation light to a read head;
(c) said read head including:
 (1) a means for shaping said shaped and filtered excitation light received from said first one of said multiple optical fiber channels;
 (2) a dichroic mirror for reflecting the excitation light shaped by said means for shaping said shaped and filtered excitation light to the top of a sample in a microplate well;
 (3) a means for shaping and filtering light emitted from said sample from the top of said microplate well; and
 (4) a light detector for measuring the amount of said shaped and filtered emitted light.

24. An analyzer of claim 23, wherein said means for shaping and filtering said excitation light comprises a first lens, for directing the excitation light to a filter, a filter for limiting the excitation light to a selected narrow band within the range of 240 to 900 nm, and a second lens for directing the filtered excitation light to said optical fiber channel.

25. An analyzer of claim 23, wherein said means for shaping the excitation light received from said optical fiber channel includes an aperture and a lens for shaping said light.

26. An analyzer of claim 23, wherein said means for shaping and filtering emitted light includes a filter, a lens, an aperture, and a light pipe.

27. An analyzer of claim 23, wherein said flash light source is selected from the group consisting of a Xenon arc lamp, a laser, and an LED.

28. An analyzer of claim 27, wherein said flash light source is a flash Xenon arc lamp.

29. An analyzer of claim 1 for analysis of a sample by fluorescence comprising:

(a) an illumination module including:
 (1) as an excitation light source, a continuous wave light source;
 (2) a means for shaping and filtering the light from said excitation light source;
(b) a second one of said multiple optical fiber channels for transmitting the shaped and filtered excitation light to the bottom of a microplate well;
(c) a third one of said multiple optical fiber channels for transmitting a read head light emitted by said sample from the bottom of said microplate well;
(d) a read head including:
 (1) a means for shaping and filtering light emitted by said sample from the bottom of said microplate well received via said optical fiber channel;
 (2) a light detector for measuring the amount of shaped and filtered emitted light.

30. An analyzer of claim 29, wherein said means for shaping and filtering said excitation light comprises a first lens for directing the excitation light to a filter, a filter for limiting the excitation light to a selected narrow band within the range of 340 to 900 nm, and a second lens for directing the shaped and filtered excitation light to said first optical fiber channel.

31. An analyzer of claim 29, wherein said means for shaping and filtering light emitted by said sample includes a filter, a lens, and a light pipe.

32. An analyzer of claim 29, wherein said emitted light received by said read head is reflected by a mirror into said means for shaping and filtering light.

33. An analyzer of claim 29, wherein said continuous light source is selected from the group consisting of a quartz halogen lamp, a continuous Xenon lamp, a deuterium lamp, a laser, and a LED.

34. An analyzer of claim 33, wherein said continuous light source is a quartz halogen lamp.

35. An analyzer of claim 1 for analysis of a sample by absorbance comprising:
  (a) an illumination module including:
    (1) as an excitation light source, a continuous light source or a flash light source;
    (2) a means for shaping and filtering the light from said excitation light source;
  (b) a second one of said multiple optical fiber channels for transmitting the shaped and filtered excitation light to the bottom of a microplate well;
  (c) a read head including:
    (1) a means for shaping light emitted by said sample from the top of said microplate well; and
    (2) a light detector for measuring the amount of said the shaped emitted light.

36. An analyzer of claim 35, wherein said means for shaping and filtering the light from said excitation light source comprises a first lens for directing the excitation light to a filter, a filter for limiting the excitation to a narrow band within the range of 340 to 900 nm, and a second lens for directing the filtered excitation light to said optical fiber channel.

37. An analyzer of claim 35, wherein said means for shaping light emitted by said sample includes a lens, and a light pipe.

38. An analyzer of claim 35, wherein said third one of said multiple optical fiber channels is a monofilament.

39. An analyzer of claim 38, wherein said third one of said multiple optical fiber channels includes a collimating lens mounted at the end of the optical fiber channel below the microplate well.

40. An analyzer of claim 35, wherein said excitation light source is selected from the group consisting of a quartz halogen lamp, a flash Xenon lamp, a continuous Xenon lamp, a deuterium lamp, a laser, and an LED.

41. An analyzer of claim 35, wherein said continuous light source is a quartz halogen lamp.

42. An analyzer of claim 35, wherein said flash light source is a flash Xenon arc lamp.

43. An analyzer of claim 35, wherein said means of (c)(1) includes a diffuser for depolarizing said emitted light.

44. An analyzer of claim 1 for analysis of a sample by luminescence comprising:
  (a) a read head including:
    (1) a means for shaping and filtering light emitted by a sample in a microplate well in response to addition of reagents;
    (2) a light detector for measuring the amount of shaped and filtered emitted light.

45. An analyzer of claim 44, further comprising a means for introducing reagents to said sample in said microplate well.

46. An analyzer of claim 44, wherein said means for shaping and filtering light include a filter, a lens, an aperture, and a light pipe.

47. An analyzer of claim 44, wherein said means for introducing reagents to said sample includes ports disposed in a lens above said sample well.

48. An analyzer of claim 1, further comprising Alpha Screen facilities.

\* \* \* \* \*